United States Patent [19]

Horn

[11] 4,072,426
[45] Feb. 7, 1978

[54] METHOD AND APPARATUS FOR DETERMINING THE REFLECTIVE PROPERTIES OF SURFACES, ESPECIALLY COATED SURFACES

[75] Inventor: Herwig Horn, Graz, Austria

[73] Assignees: Pluss-Staufer AG, Oftringen, Switzerland; Zentrum fur Elektronemikroskopie, Graz Steyrergasse, Austria

[21] Appl. No.: 495,576

[22] Filed: Aug. 8, 1974

[30] Foreign Application Priority Data

Jan. 17, 1974 Germany .............................. 2402127

[51] Int. Cl.$^2$ ............................................. G01N 21/48
[52] U.S. Cl. .................................... 356/212; 356/210; 356/104
[58] Field of Search ............... 356/209, 210, 212, 204, 356/104; 250/237 R

[56] References Cited

U.S. PATENT DOCUMENTS

| | | | |
|---|---|---|---|
| 2,378,433 | 6/1945 | Rezdorfer | 356/221 |
| 3,310,680 | 3/1967 | Hasegawa | 356/104 |
| 3,565,568 | 2/1971 | Hock | 356/212 |
| 3,571,291 | 7/1971 | Greer et al. | 356/212 |
| 3,804,521 | 4/1974 | Sprague | 356/210 |
| 3,835,315 | 9/1974 | Gravatt | 356/103 |
| 3,850,526 | 11/1974 | Corey | 356/209 |

FOREIGN PATENT DOCUMENTS 466,114  6/1950  Canada .................................. 356/210

OTHER PUBLICATIONS

Hunter et al., "A Gloss Test for Waxed Paper", TAPPI, vol. 39, No. 12, Dec. 1956, pp. 833–841.
Hunter; Richard S., "Methods of Determining Gloss", Research Paper RP958, Journal of National Bureau of Standards, vol. XVIII, Jan. 1937.

*Primary Examiner*—John K. Corbin
*Assistant Examiner*—R. A. Rosenberger
*Attorney, Agent, or Firm*—Albert L. Jeffers

[57] ABSTRACT

A method and apparatus for determining the reflective characterstic of surfaces, especially coated surfaces, in which a beam of parallel light rays are directed against the surface at a predetermined angle of incidence. The light rays reflecting from the surface at an angle numerically equal to the angle of incidence are caused to converge and are supplied to a receiver which may be in the form of a light sensitive resistor. The light which scatters from the surface by reflecting therefrom at angles numerically different from the angle of incidence are, at least in part, collected and caused to converge and are supplied to a second receiver which may also be in the form of a light sensitive resistor. The changes in values of the resistors when illuminated in the aforesaid manner are compared and thereby a comparison is arrived at of how much light is reflected directly from the surface and how much light is scattered during reflecting.

11 Claims, 1 Drawing Figure

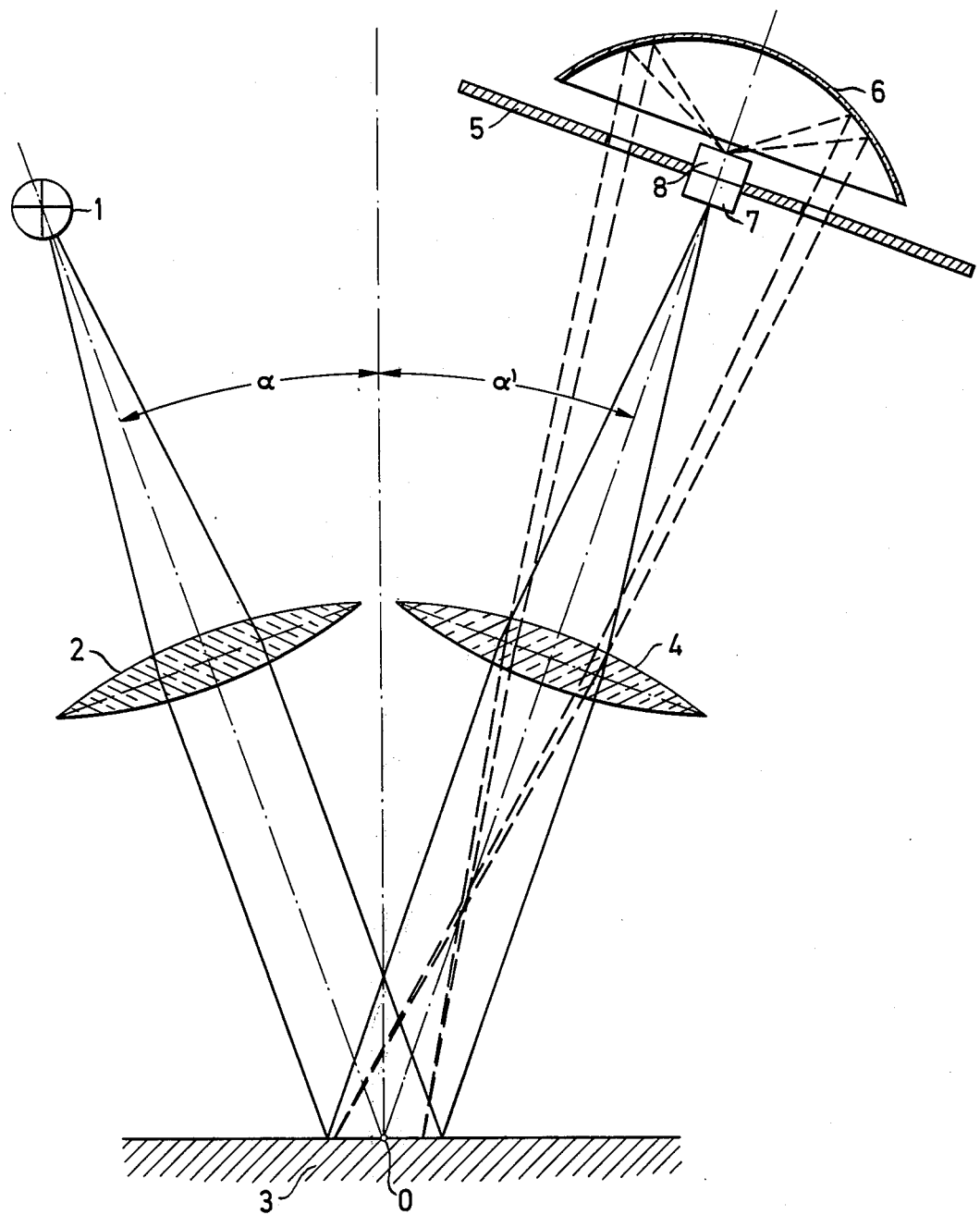

METHOD AND APPARATUS FOR DETERMINING THE REFLECTIVE PROPERTIES OF SURFACES, ESPECIALLY COATED SURFACES

The present invention relates to the measuring of the reflective characteristics of a surface, especially a coated surface, and the establishing of a system for evaluating the reflective characteristics of such surfaces.

At the present time, the procedure for measuring the reflective characteristics of a surface, especially a coated surface, is to view the surface optically and to arrive at an evaluation in this manner.

Obviously, such a method involves considerable variation because different observers receive different effects. The directly reflected light, which is to say, the light reflected from a surface at an angle of reflection which is equal to the angle of incidence, gives an impression of the gloss of the surface, but the light reflected at different angles is less easy to evaluate because it appears as a more or less diffused halo about the directly reflected light.

It is known that the gloss of lacquered surfaces, and surfaces similar thereto, may be measured by devices of various types. See PLASTE UND KAUTSCHUH 16, No. 5, starting Page 366 (1969); FARBE UND LACK 70, No. 9, starting Page 693 (1964); ibid. 79, No. 3, starting Page 191 (1973). It is also known why a surface develops a fog or haze or halo due to light scattering. In this connection, reference may be made to FARBE UND LACK 73, No. 7, starting Page 625 (1967).

Attempts, which have, heretofore, been unsuccessful, to develop a measuring procedure for measuring the optical fog from coated surfaces are referred to at FARBE UND LACK, No. 7, starting Page 625 (1967); PLASTE UND KAUTSCHUK 16, No. 5, starting Page 366 (1969); FARBE UND LACK 74, No. 2, starting Page 145 (1968); Progress in Organic Coatings, I, starting Page 113 (1972).

With the foregoing in mind, a primary object of the present invention is the provision of a method and apparatus for effecting the measurement not only of the reflective characteristics of a surface, especially a coated surface, but also of the amount of indirectly reflected light which comes off the surface at angles different from the angle of incidence thereof.

BRIEF SUMMARY OF THE INVENTION

The problems underlying the present invention were solved by separately collecting the light reflected from a surface at the angle of incidence of the light falling on the surface and at least a portion of the light reflected from the surface at angles different from the angle of incidence, separately causing convergence, or condensing, of the two portions of the light thus collected and directing the condensed portions to receivers arranged to provide a numerical value for the surface being measured indicative of the characteristics thereof.

Preferably, the receivers are in the form of light sensitive resistors and are connected in a Wheatstone bridge circuit for comparing the changes in values of the resistors when illuminated and, therefore, comparing the amounts of light falling thereon.

The device according to the present invention is characterized in the provision of a source of light, preferably laser light, a converging, or condensing, lens for creating a beam of parallel light rays, a converging, or condensing, lens for receiving the light which reflects from the surface being measured at an angle equal to the angle of incidence, a receiver for receiving the condensed light from the lens; an annular lens opening surrounding the condensed light, and an arrangement for condensing the light passing through the annular opening, and another receiver for receiving the last mentioned light.

The annular lens opening may be in the form of a diaphragm system and is coaxial with the condensed reflected light beam and is larger in diameter than the condensed reflected light beam so that only those light rays which reflect from the surface at angles different from the angle of incidence of the primary light beam will pass through the annular lens opening.

The receivers referred to, as mentioned, are advantageously light sensitive resistor elements, but may be other photoelectric devices.

The nature of the present invention will be more fully understood upon reference to the following detailed specification taken in connection with the accompanying drawing which schematically illustrates a device according to the present invention and adapted for practicing the method of the present invention.

DETAILED DESCRIPTION OF THE INVENTION

The light source in the drawing is indicated at 1, and this light source falls on a condensing or converging lens 2 and emerges therefrom in the form of a beam of parallel light rays which falls in that manner on the surface of sample 3 which is to be measured. The light reflects from surface 3 with the principal portion leaving the surface 3 at an angle $\alpha'$ which is numerically equal to the angle of incidence $\alpha$ of the light falling on the surface.

The regularly reflected light rays, which is to say, the light rays which reflect from the surface at an angle numerically equal to the angle of incidence thereof, are shown in full lines in the drawing while the light rays reflecting from the surface at angles different from the angle of incidence of the primary light beam are indicated in dashed outline.

A second converging or condensing lens is indicated at 4 and this lens condenses the principal reflected light beam so that it falls on a receiver 7 which, as mentioned, is preferably in the form of a light sensitive resistor.

The scattered light, indicates by the dashed lines, is intercepted by an annular diaphragm member 5 which is coaxial with the optical axis of condensing or converging lens 4 and which may be disposed in surrounding relation to receiver 7. The diffused light passing through the annular opening of diaphragm 5 is reflected by the concave mirror 6 so as to fall on a receiver 8 and which also may be a light sensitive resistor and may even form a unit with resistor 7.

The source of light beam represented by light source 1 and condensing or converging lens 2 and the receiving system represented by lens 4, diaphragm 5, mirror 6 and receivers 7 and 8 may be adjusted to vary the angles $\alpha$ and $\alpha'$ provided these two angles always remain numerically equal to each other.

By measuring the radiation intensity IR in the receiver 7 and the radiation intensity ID in the receiver 8, and by coupling these measured values electrically, as in a Wheatstone bridge circuit, a single measured value can be arrived at for the amount of irregularly reflected, or scattered, light from the surface. This scattered light might be referred to as gloss-fog or haze.

In another embodiment of the invention, there may be a frosted glass plate disposed directly behind the annular diaphragm 5 and which plate will become illuminated by light passing through the annular opening in the diaphragm. This light can then, in turn, be condensed or caused to converge in any suitable manner on a receiver and the intrinsic value thereof obtained. This light, which will be in the form of a ring, can be condensed so as to fall upon a single measuring cell.

Both components of the reflected light could be measured by a single cell but only if a shutter is employed to interrupt the portion of the light not being measured.

It is possible within the scope of the invention to measure simultaneously the gloss-fog and the gloss by arriving at a value for only the intensity IR for the gloss and proceeding in the aforesaid manner for arriving at a value for the gloss-fog, or haze.

The device of the present invention and the method described is suitable for measuring the optical characteristics with painted and coated surfaces, such as lacquered surfaces and also for measuring surfaces on which plastics have been deposited. In each case, the optical characteristics of the surface is an indication of the quality thereof.

Since the characteristics being measured according to the present invention are subjective impressions created in the eye of the observer, it was necessary to arrive at calibrated standards for use in connection with the device. To obtain such calibrated standards, a series of samples were arranged according to the degrees of haze formation. This series of standards was arrived at by a number of skilled observers visually and operating independently of one another.

It has been found that, in most cases, the measurement can be done with a constant angle of 20° for each of α and α', as shown in the drawings, and only in extreme cases, for example, when the gloss-haze is extremely strong, is it necessary to increase the angles up to as much as, for example, 60°.

A standard scale was established by utilizing lacquers of various glosses on calibration samples and the samples were calibrated in steps rising from 1 to 10. These samples were placed in the device with angles α and α' equal to 20°. Two photosensitive resistors having the same characteristic curves were employed as the receivers 7 and 8 were connected as respective branches in a Wheatstone bridge circuit so that the measuring instrument in the circuit would, at all times, show the ratio of the values of the resistances of the photosensitive resistors.

For the example referred to for this resistance ratio RQ, the values obtained are shown in the accompanying chart.

SAMPLE MEMBER (Arranged according to gloss-fog as determined by visual inspection)

| (Ratio, RQ) | 1 | 2 | 3 | 4 | 5 | 6 | 7 | 8 | 9 | 10 |
|---|---|---|---|---|---|---|---|---|---|---|
| | 0.34 | 2.7 | 4.3 | 6.5 | 7.0 | 10.1 | 12.1 | 14.9 | 25.0 | 33.5 |

With the values indicated in the chart which are established by the selected standard samples, the degree of gloss-fog of other lacquer samples may now be read out directly by inserting a sample in the machine and reading the values from the indicating instrument in the bridge circuit in which the photosensitive resistors are connected.

Thus, for example, for a series of measures consisting of 5 samples, there may be read the RQ values of 4.5, 6.8, 10.4, 15.5 and 33 which correspond respectively to the degrees of gloss—fog, haze, or blush of 3, 4 to 5, 6, 8 and 10.

The diaphragm arrangement 5 shown on the drawings had, for purposes of making these measurements, a circular annular opening with radii of 12.5 and 22.5 millimeters. The light source employed was a helium-neon laser of two kilowatts output.

In order to be able to produce the measured values, there was employed polished plates of fused quartz which were etched by hydrochloric acid to a desired degree of dullness.

What is claimed is:

1. The method of determining the reflective characteristics of a surface, especially a coated surface, which comprises; directing a bundle of parallel light rays against a substantial area of the surface at a predetermined angle of incidence, condensing with a first condensing means first light rays which reflect from said surface at an angle of reflection numerically equal to said angle of incidence, simultaneously condensing with a second condensing means second light rays that reflect from said surface at an angle which is numerically different from said angle of incidence and disposed in surrounding relation to the condensed first light rays which have passed through said first condensing means and falling within predetermined inner and outer radial limits, intercepting the condensed first and second light rays by respective light sensitive electrical components, and comparing the changes in value of said components to arrive at a value for the reflective characteristics of said surface.

2. The method according to claim 1 in which said light is coherent light from a laser and the first condensing means is a condensing lens having a diameter greater than the diameter of the parallel light beam reflected from the surface.

3. The method according to claim 1 which includes developing said light by a light source, condensing the light from said source into a beam of parallel light rays, condensing the first light beam which reflects from said surface at an angle numerically equal to the angle of incidence of the light from said source on said surface via a condensing lens having a diameter greater than the diameter of the parallel light beam reflected from the surface, disposing an annular lens opening around the condensed reflected first light beam coaxially therewith, the smaller diameter of said annular lens opening being larger than the diameter of said condensed first light beam at the same axial point along the condensed first light beam, condensing the scattered light which passes through said condensing lens and then through said annular lens opening, disposing a respective light sensitive resistor in intercepting relation to each of the said condensed reflected first light beam and the condensed scattered light, and comparing the changes in values of the resistors thereby to compare the values of the light falling thereon.

4. A device for determining the reflective characteristics of a surface, especially a coated surface, which comprises; a light source for directing a beam of parallel light rays against a predetermined substantial area of the surface at a predetermined angle of incidence, a condensing lens for condensing first light which reflects from said surface at an angle numerically equal to the said angle of incidence, said condensing lens having a diameter greater than the diameter of the parallel light beam reflected from the surface, an annular lens opening and condensing means for receiving and condensing at least a portion of second light which is reflected from said surface at angles numerically different from said angle of incidence and which second light passes through said condensing lens and surrounds the first light condensed by said condensing lens, and respective light sensitive receivers disposed to intercept the light condensed by said condensing lens and the light which passes through said annular lens opening and condensing means, respectively.

5. A device according to claim 4 in which said receivers are in the form of respective light sensitive electrical components.

6. A device according to claim 5 in which said components are light sensitive resistors.

7. A device according to claim 6 in which said resistors are adapted for connection into a bridge circuit.

8. A device according to claim 4 in which said condensing lens and said annular lens opening and condensing means and said receivers are rigidly interconnected.

9. A device according to claim 4 in which said annular lens opening and condensing means comprises an annular lens opening coaxial with and radially spaced from the light condensed by said condensing lens, and a concave mirror disposed to intercept and to condense the light passing through said annular lens opening.

10. A device according to claim 9 in which said annular lens opening is formed by diaphragm lens means.

11. A device according to claim 4 in which said light source includes a laser and a condensing lens.

* * * * *